United States Patent
Gross et al.

[11] Patent Number: 6,045,583
[45] Date of Patent: Apr. 4, 2000

[54] TWIN-SHELLED ARTIFICIAL HIP JOINT AND ITS MANUFACTURE

[75] Inventors: Walter Gross, Ossingen; Kurt Bider, Winterthur; Jürg Oehy, Henggart, all of Switzerland

[73] Assignee: Sulzer Orthopaedie AG, Baar, Switzerland

[21] Appl. No.: 09/046,375

[22] Filed: Mar. 23, 1998

[30] Foreign Application Priority Data

Mar. 25, 1997 [EP] European Pat. Off. ............ 97810176

[51] Int. Cl.[7] ............................................. A61F 2/32
[52] U.S. Cl. ................................................. 623/22
[58] Field of Search ............................. 623/22, 18, 16

[56] References Cited

U.S. PATENT DOCUMENTS

| | | | |
|---|---|---|---|
| 4,685,923 | 8/1987 | Mathys | 623/22 |
| 4,828,565 | 5/1989 | Duthoit et al. | 623/22 |
| 5,755,806 | 5/1998 | Stalcup et al. | 623/22 |

*Primary Examiner*—Mickey Yu
*Assistant Examiner*—Alvin Stewart
*Attorney, Agent, or Firm*—Townsend and Townsend and Crew LLP

[57] ABSTRACT

The invention shows a hip joint socket and its manufacture, with the hip joint socket including a thin walled metallic outer shell with anchoring pins which is firmly connected to an inner shell of plastic. Since the bearing surface of the inner shell is not produced until after the assembly, a high accuracy of shape of the bearing surface results together with a relatively elastic outer shell and with good anchoring aids for a primary anchoring.

11 Claims, 6 Drawing Sheets

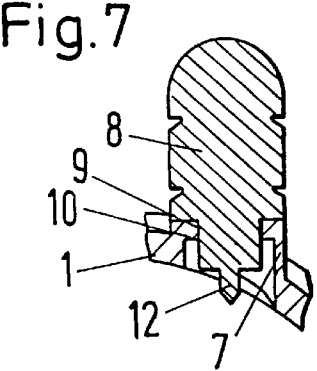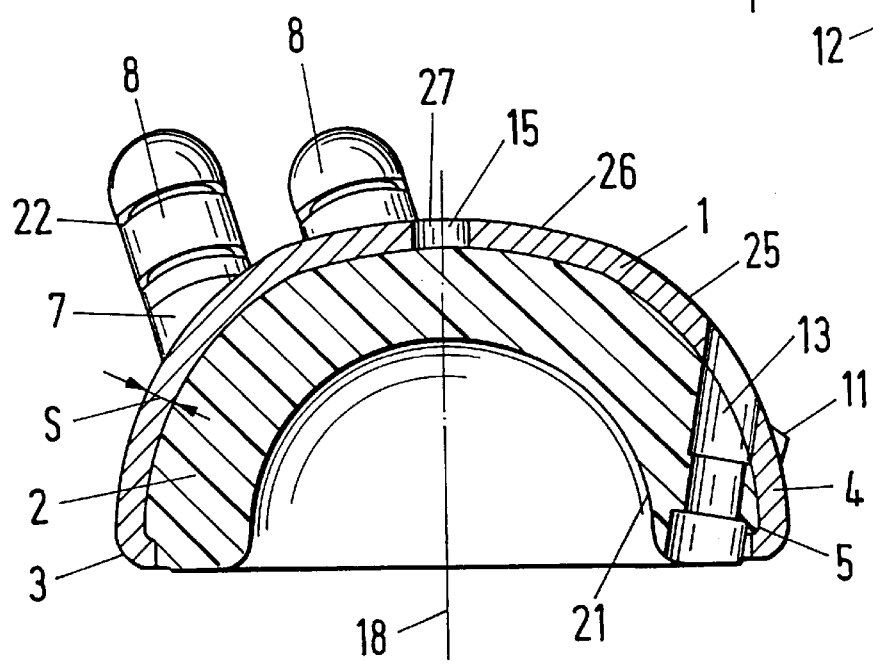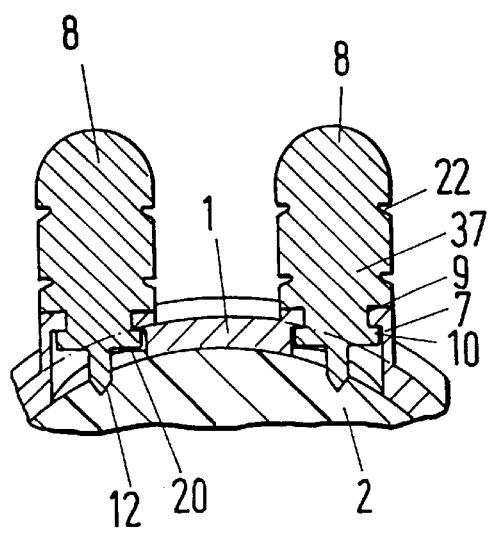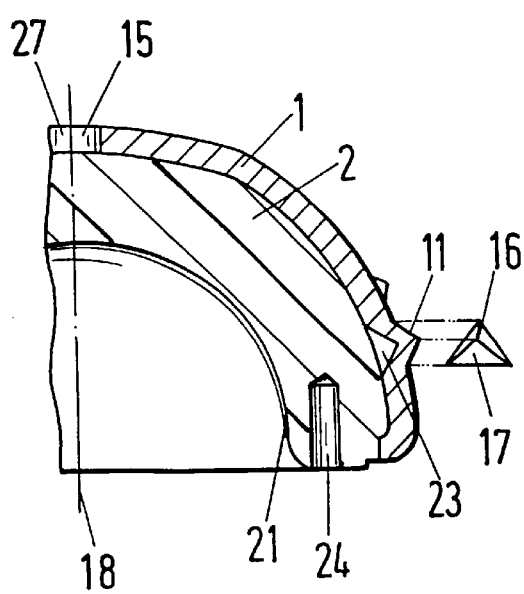

TWIN-SHELLED ARTIFICIAL HIP JOINT AND ITS MANUFACTURE

BACKGROUND OF THE INVENTION

The invention relates to a twin-shelled artificial hip joint socket with an outer shell of titanium and an inner shell of high molecular compressed polyethylene, with the outer shell projecting inwardly beyond the inner shell in the region of the equator to such an extent that a permanent connection exists between the shells which can no longer be released.

DESCRIPTION OF THE PRIOR ART

A hip joint socket in which the outer shell consists of metal and the inner shell consists of polyethylene is shown in U.S. Pat. No. 5,080,677. The outer shell is anchored in a pelvic bone which has been prepared for it, with it also being possible to use bone screws as aids which can be drawn into the pelvic bone through apertures in the outer shell. The inner shell has an oversize with respect to the outer shell at room temperature which diminishes through cooling down of the inner shell and corresponding contraction of the inner shell to such an extent that the cooled inner shell can be implanted intra-operatively and produces a press fit through its expansion on attaining a body temperature of 37° C. which also brings the plastic to flow into undercuts in the outer shell in order to thus produce a permanent connection.

Furthermore, EP-A-0 699 425 discloses, among other things, a hip joint shell with an outer shell of titanium which is rolled in at its equator about an inner shell of polyethylene with an inwardly standing countersurface. Furthermore, there are pins which are radially anchored in outer shells by a clamping connection (U.S. Pat. No. 5,226,917). This presupposes, however, a thick walled outer shell with all its manufacturing disadvantages.

SUMMARY OF THE INVENTION

The object of the present invention is to provide a prosthesis which can be mass produced economically and which can be anchored well.

This object is satisfied by the outer shell which is formed of a deep drawn sheet metal sheet with a thickness $3>s>1$ mm; wherein the outer shell is rolled in about a shoulder of the inner shell by a bending or rolling in process; and wherein the outer shell has at least one protrusion approximately in a main stress direction with an anchoring pin fastened thereto.

An advantage of the invention lies in a broad range of use, since it can be used in a relatively large number of cases. A further advantage lies in the fact that hardened polyethylene types, which contain a higher degree of polymerization and fewer radicals through irradiation with electrons or γ-rays and a heat treatment, can be used without problem for inner shells with the manufacturing process indicated, since neither the exactness of the form of the bearing surface is impaired, nor is a flow of polyethylenes into the outer shell presupposed. With a polyethylene, which has a significantly lower rate of wear, it is in many cases no longer necessary to make an inner shell replaceable. This not only has the result that re-operations due to reasons of wear are unnecessary, but also that the design of the bond can be optimized with respect to better functional behavior. It has been proven that a thin outer shell of titanium represents a low resistance between an elastic inner shell of polyethylene and an elastic bone bed. Thus, the outer shell should be able to follow the resultant deformations between the inner shell and the bone bed and nevertheless be capable of good primary and secondary anchorage. As a kind of optimum or best compromise, an outer shell has resulted which is manufactured of a deep drawn sheet metal sheet of titanium with a thickness $3>s>1$ mm and is worked in accordance with the method described in the following, with a sheet metal thickness of 2 mm being preferred. A round blank of deep, drawn sheet metal sheet is pressed with a punch into a die and receives the form of a shell with a cylindrical extension. After the workpiece has been ejected, the run-in collar in the cylindrical part is separated from the outer shell, for example by turning, with a cylindrical edge being left standing on the shell. For better centering of the outer shell in succeeding operations, a centering bore can be placed at the pole of the outer shell.

One or more protrusions are formed out on the outer shell and inner shoulders for the later attachment of the anchoring pins which are formed with further pressing tools. Further projections in the form of teeth can be formed out which are an aid during the primary anchoring of the outer shell in a bone bed.

Prior to the pressing out of the definitive form of the protrusions, it can be advantageous to reduce the prestresses by an intermediate annealing. Bores are placed in the protrusions into which the anchoring pins are pushed from the outside in order to rivet them together with the inner shoulders of the protrusions.

Through the use of a hollow, rocking riveting tool the anchoring pins can be formed in such a manner that a positioning tip for the later, inner shell remains standing on the inner side.

Through the use of a deep drawn metal sheet for the outer shell it is also possible to point weld preformed metallic meshes on the outer shell, for example, in the region of the anchoring pins in order to facilitate the ingrowth of bone tissue.

For the later inner shell, a round blank of wear resistant plastic, for example of hardened high molecular polyethylene, is provided with an outer contour which corresponds to the inner contour of the outer shell with the exception of a set-back step in the equatorial region of the cylinder. The round plastic body is now pressed into the outer shell in a tool and at the sane time the cylindrical edge of the outer shell is firmly connected to the later inner shell by bending or flanging. Through a preheating of the outer shell far above the sterilization temperature, the material of the round body, when being pressed, can also flow into the cavities which have arisen on the outer shell during the forming of projections. This has the advantage that no cavities remain which could encourage the settling of microbes.

The round body, which is firmly connected to the outer shell, is machined to a finished bearing shell on the inner side through chip forming machining. In addition, bores for bone screws can be made in the end face of the inner shell, with the outer shell being opened for this purpose from the outside with a suitable milling tool.

The hip joint shells described here and their manufacture have the advantage that they are suitable for an economical production in large quantities. A further advantage is that the connection of anchoring pins to a very thin outer shell takes place under controlled workshop conditions, i.e. without the influence of the surgeon. It is furthermore advantageous that the outer shell can be kept so thin that it can better follow the deformations of the bone bed and the inner shell.

BRIEF DESCRIPTION OF THE DRAWINGS

FIG. 4 is an enlarged schematic section through the hip joint shell of FIG. 3;

FIG. 5 is an enlarged schematic section through the hip joint shell of FIG. 2 with two anchoring pins;

FIG. 6 is a schematic section displaced with respect to FIG. 4 with pressed out protrusions in the form of teeth;

FIG. 7 is an enlarged schematic section of an anchoring pin placed into a protrusion prior to riveting;

DETAILED DESCRIPTION OF THE PREFERRED EXEMPLARY EMBODIMENTS

Figure 1:
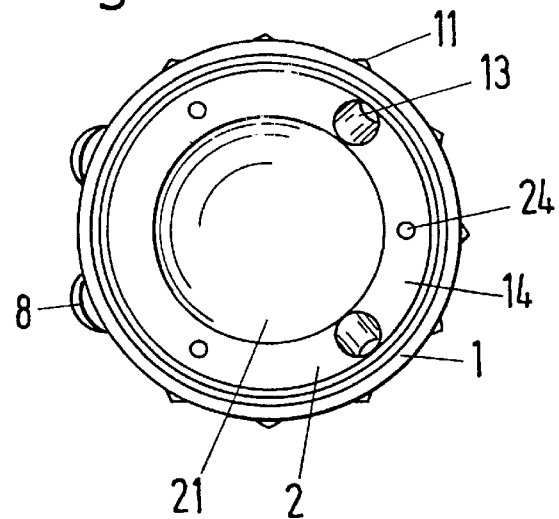
FIG. 1 is a schematic lower view of a hip joint shell in accordance with the invention.
Figure 2:
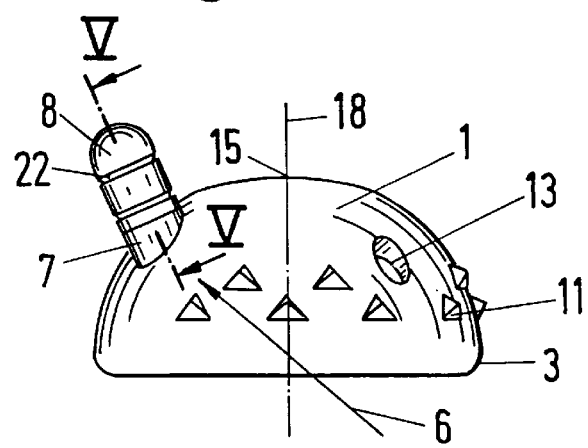
FIG. 2 is a schematic side view of the hip joint shell of FIG. 1.
Figure 3:
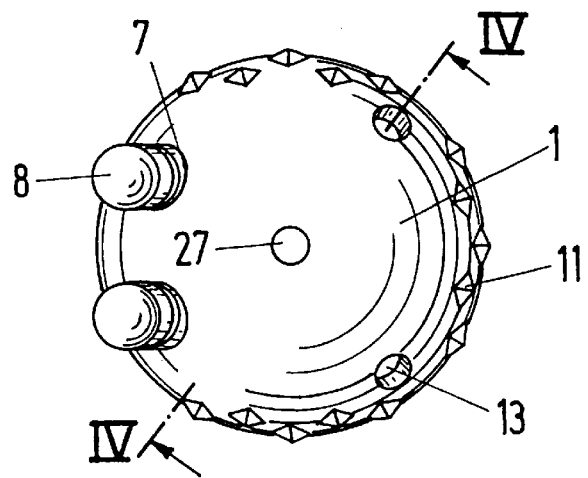
FIG. 3 is a schematic plan view of the hip joint shell of FIG. 1.

A hip joint shell and its manufacture are shown in the figures, with the hip joint shell consisting of a thin walled metallic outer shell 1 with anchoring pins 8 which is firmly connected to an inner shell 2 of plastic. Since the bearing surface 21 of the inner shell 2 is not produced until after the bonding, a high accuracy of shape of the bearing surface results together with a relatively elastic outer shell and with good anchoring aids for a primary anchoring.

FIGS. 1, 2, 3 and 4 show a hip joint shell with an outer shell 1 and an inner shell 2 rolled in within it. The outer shell 1 consists of a deep drawn metal sheet 4 of titanium with a thickness S of 2 mm. Two protrusions 7 are pressed out of the roof of the outer shell 1, each of which form a pedestal for a firmly connected anchoring pin 8. The anchoring pins 8 are arranged parallel to one another and are turned parts of titanium which have indentations 22 for better anchoring in the bone. The protrusions 7 are provided in the region of a principal load force 6. The inclination of the anchoring pins 8 to the polar axis 18 is chosen in such a manner that the shell 1 can follow the direction of the pin 8 when being inserted into the bone bed. Teeth 11 are pressed out above the equator 3 of the outer shell and serve for an improved primary anchoring. Inclined bores 13 pass from the front face 14 of the inner shell 2 through the outer shell 1 in order to assist the anchoring by means of bone screws which can be placed therein. A centering and inspection opening 27 is placed at the pole 15 of the outer shell 1 in order to be able to centre the outer shell and to inspect the bonding of the outer and inner shell. Three receiving bores 24 are placed at the front face 14 of the inner shell 2 in order to be able to pick up the finished shell 1, 2, with a setting tool. The inner shell 2 has a spherical bearing surface 21, whereas its outer surface, just as that of the outer shell 1, has a spherical surface 25 with a flattened portion 26 in the pole region 15. A shoulder 5 is recognizable in FIG. 4 in the region of the equator 3 about which the outer shell 1 is rolled in.

In FIGS. 7 and 5, the position of the anchoring pin 8 prior to and after riveting to a protrusion 7 of the outer shell 1 can be seen. The anchoring pin 8 is pushed into place at a bore 9 of the protrusion 7 and projects into the outer shell past the inner shoulder 10, with a positioning tip 12 for the later inner shell 2 projecting the furthest. During the actual riveting process, the material is plastically deformed about the positioning tip towards the inner shoulder 10 in order to form a firm assembly with the latter by means of a rivet head 20. The anchoring pin 8 must be pushed on from the outside because it projects with its head 37 beyond the bore 9 up to the outer diameter of the protrusion 7.

In FIG. 6, an additional section through a tooth 11 is shown which is pushed out from the outer shell and has the form of a triangular pyramid, with an edge being oriented as a cutting edge 16 towards the pole 15 and a flat side 17 being directed towards the equator. Prom the pushing out of the tooth 11, a cavity 23 has remained at the inner side of the outer shell 1.

Various tools for the manufacture of the hip joint shell 1, 2 will be described with respect to the FIGS. 8 to 13.

Figure 8:
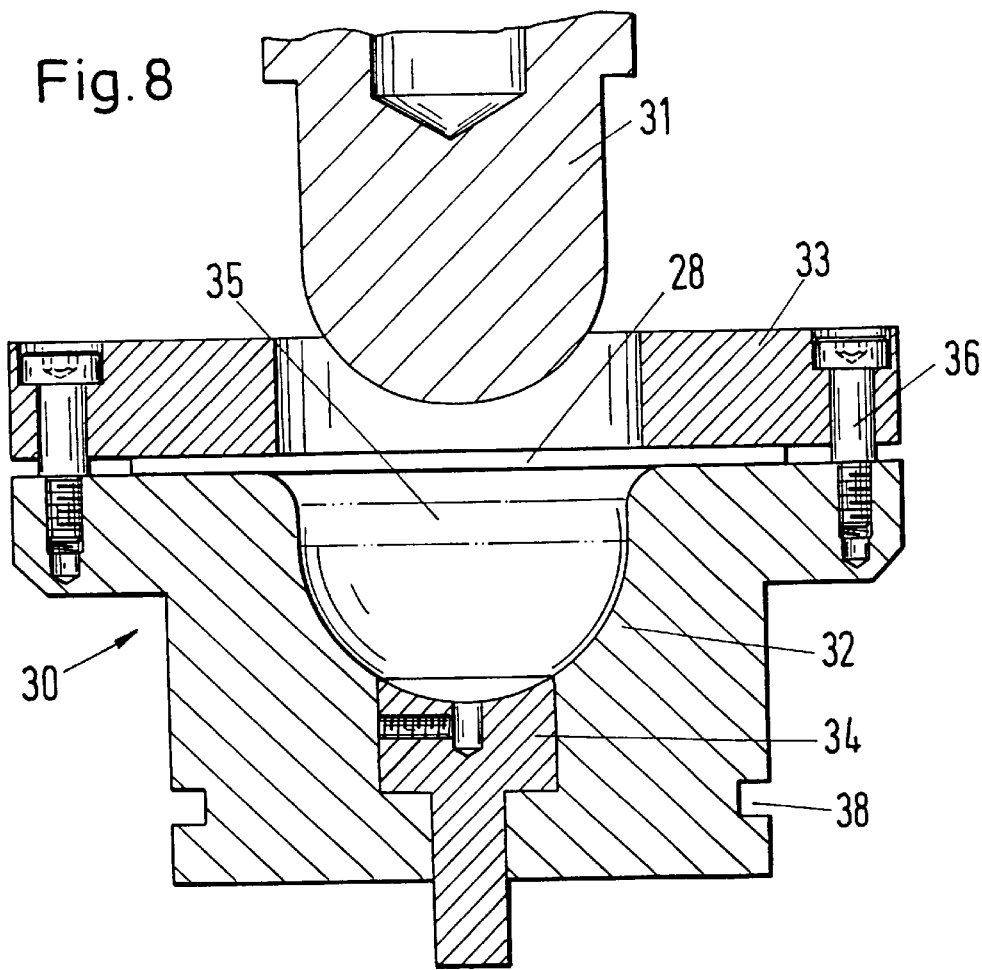
FIG. 8 is a schematic section through a deep drawing tool for the production of a thin walled outer shell.

In FIG. 8, a metal sheet 28 of deep drawing grade is laid in a deep drawing tool 30. The tool consists of a punch 31 and a die 32 which is completed at its bottom by an ejector 34. A hold down member 33 is fastened to the die 32 by fastening screws 36. The inner side of the die 32 has a spherical region to which a cylindrical region 35 adjoins. After the deep drawing, the outer shell is parted from the blank in this region 35, with a cylindrical collar 29 remaining standing for the later rolling in at the outer shell.

Figure 9:
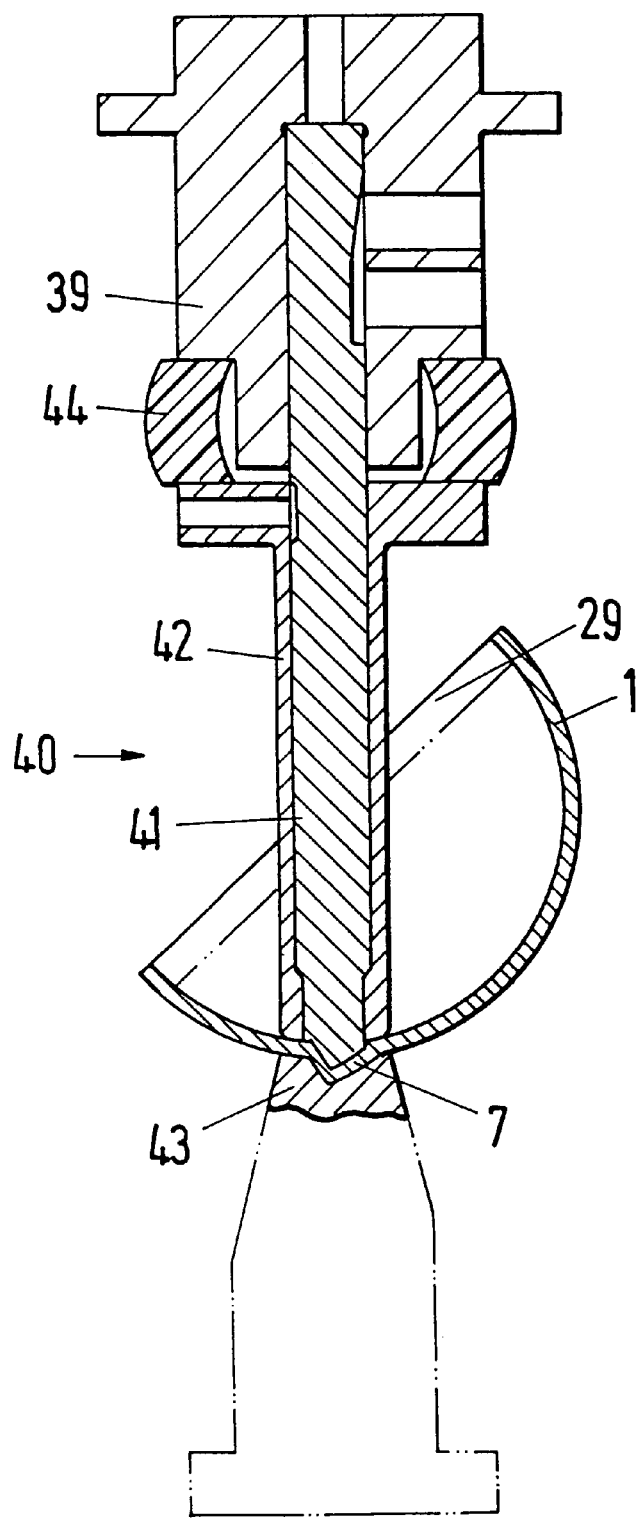
FIG. 9 is a schematic section through a deep drawing tool for the production of protrusions on a metallic outer shell.

FIG. 9 shows a deep drawing tool 40 with a die 43 which has the form of the protrusion 7 and with an upper tool part 39. At the upper tool part, a hold down member 42 is biased against an outer shell 1 which has been laid in place by a spring element 44 before a punch 41 presses the sheet metal into the die 7 and thus produces a protrusion 7 in its raw form. Since two protrusions 7 are arranged parallel to one another but have no common plane through the pole axis, each of the two protrusions 7 requires its own tool.

Figure 10:
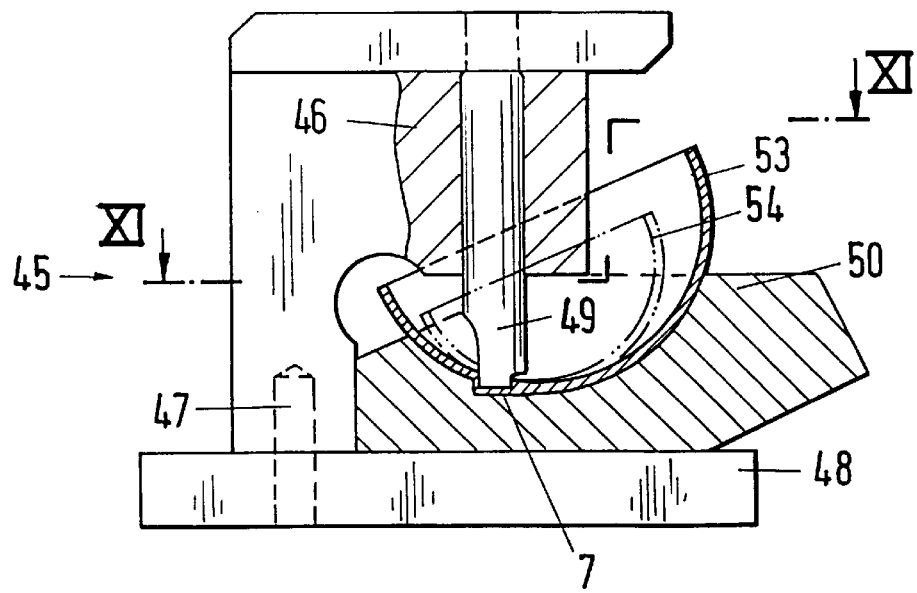
FIG. 10 is a schematic section through a pressing tool for the forming out of two parallel protrusions.
Figure 11:
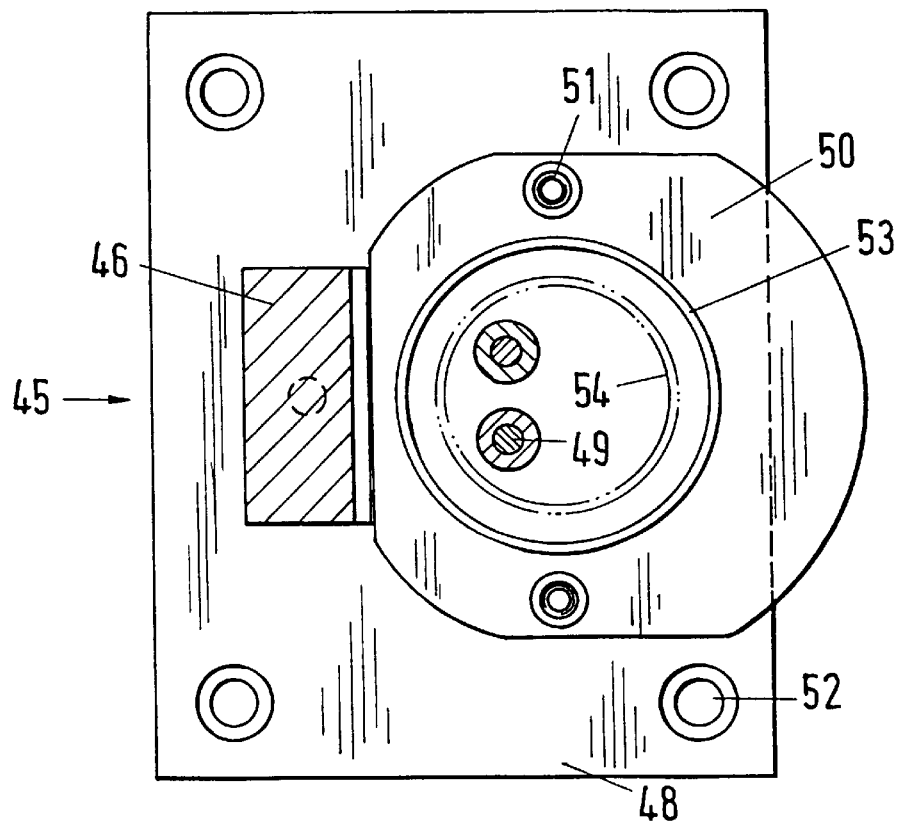
FIG. 11 is a schematic cross-section through the upper tool part and a plan view of the lower tool part of the pressing tool in FIG. 10.

FIGS. 10 and 11 show a pressing tool 45 for the final forming of two protrusions 7. A large outer shell 53 is placed in a die 50, which is in turn connected to a lower tool part 48 by screw connections 51. An upper tool part 46 is precentered via a pin 4 and the die 50. Two punches 49 are integrated in the upper tool part 46 which press out the final form of the protrusions 7 with accurate dimensions. For a smaller outer shell 54 the die 50 is replaced, whereas the punches 49 can remain in place. Prior to the final pressing out of the protrusions 7 it can be necessary to subject the outer shell to an intermediate heat treatment or annealing process. The pressing tools 30, 40, 45 are mounted in a press, for example in a 4-pillar press, with fastening screws 52 or reception grooves 38. The bores 9 in the protrusions 7 as well as the centering bore 27 at the pole 15 are most simply bored with a drilling jig.

Figure 13:
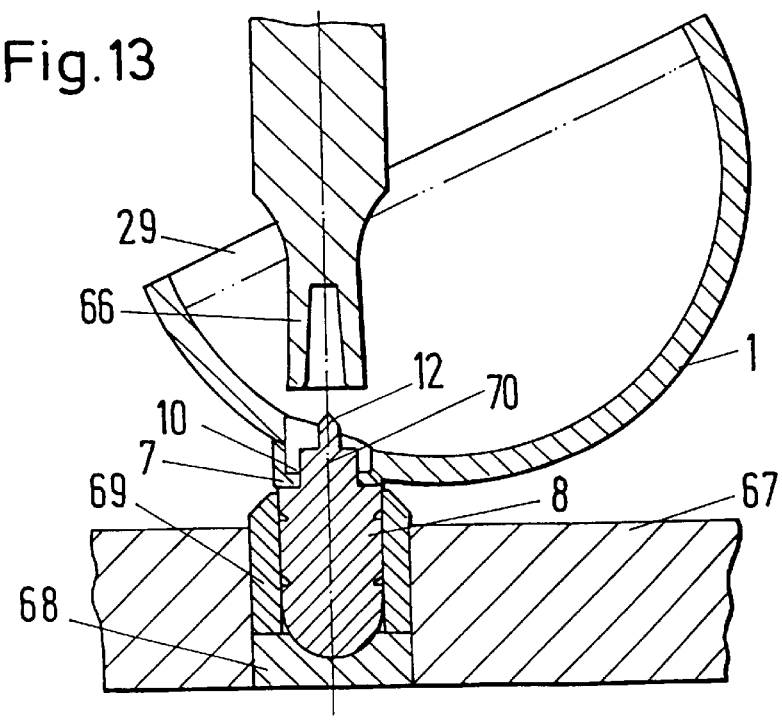
FIG. 13 is a schematic riveting tool and a holding tool for the riveting of anchoring pins to a protrusion of a thin walled outer shell.

FIG. 13 shows the riveting of the anchoring pin 8 to the outer shell 1. An anchoring pin 8 is inserted in a receiving apparatus 67, which contains a pressure part 68 and a guide bush 69, and the outer shell 1 with the protrusion 7 is pushed over it and held down. A riveting tool 66, which makes a rocking or swashing movement about its own axis without rotating about its own axis, is advanced in the direction towards the pin axis 70. The inner side of the riveting tool 66 has a cut-out in order that the positioning tip 12 of the anchoring pin remains undamaged in spite of the rocking movement. The shoulder outside the positioning tip 12 is hammered down to such an extent by the riveting tool 66 that a rivet head 20 forms on the inner shoulder 10. After the riveting process, a crack test can be performed on the outer shell and surfaces can be bead blasted and cleaned. The protrusions 7 can also be finely blasted and cleaned prior to the riveting.

Figure 12:
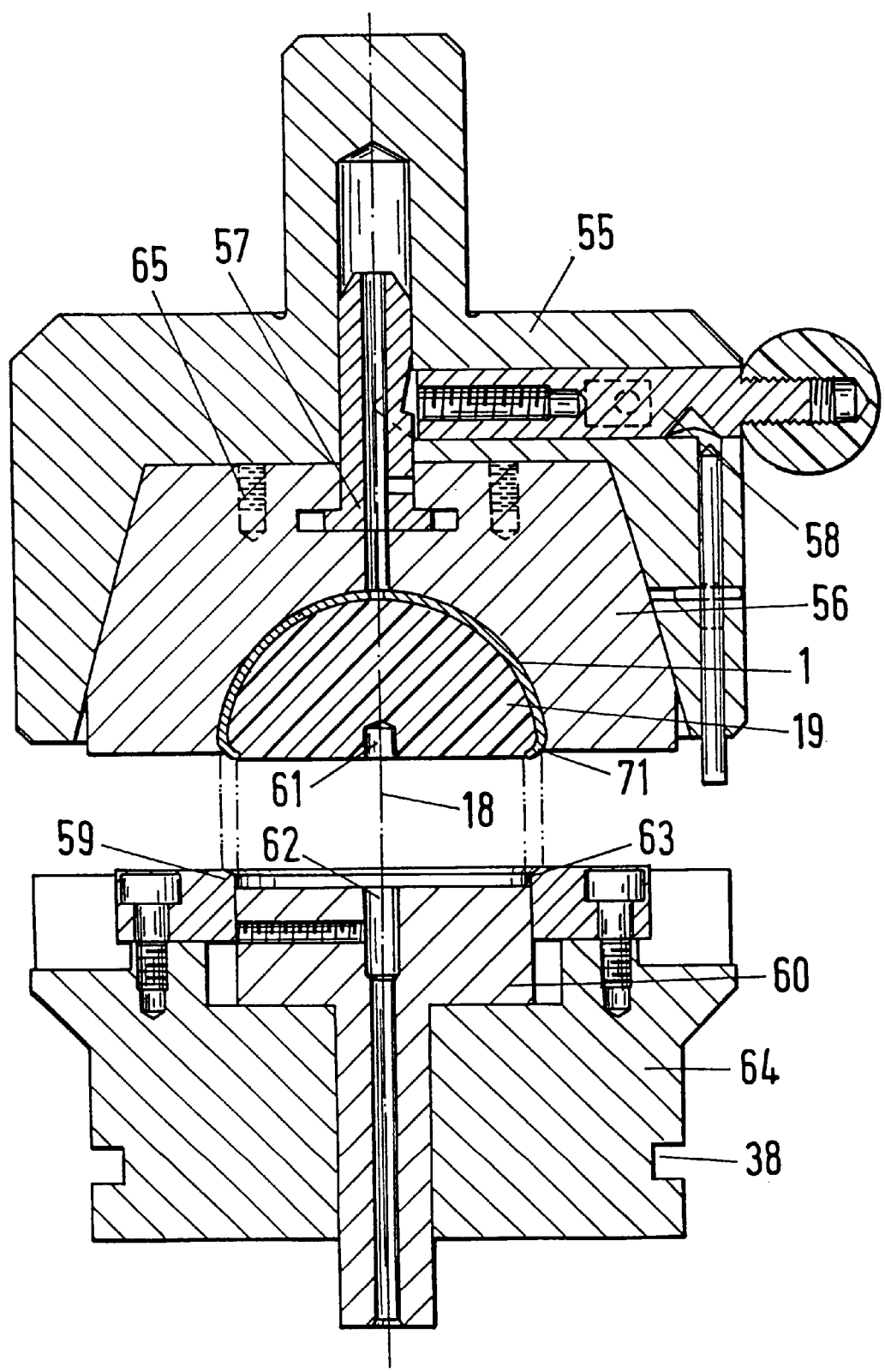
FIG. 12 is a schematic pressing and rolling in tool for connecting a deep drawn outer shell to a later inner.

In the tool of FIG. 12, the actual rolling in of the outer shell 1 about a round body 19 is provided, the outer contour of which corresponds to the outer shell with the exception of the cylindrical collar 29 which projects over a shoulder 5 at the equator 3 prior to the rolling in. The round body 19 consists of solid material, a wear resistant plastic such as, for example, hardened high molecular polyethylene. The upper tool part 55 has a fourfold divided form part 56 the inserts of which are displaceable along inclined surfaces, with the inserts being held at the same level by a guide device 57 and moved towards the center when the tool is moved together. Holding screws 65 prevent the inserts from falling out. The guide device 57 can in turn be locked and unlocked in the closed position via a latching mechanism 58. A punch 60 is journalled in the lower tool part 64 and bounded outwardly by a form ring 59. For the insertion of the round body 19 and the outer shell 1 the punch 60 projects over the form ring 59, the upper tool part is lifted off and the inserts 56 hang in their lowest position and lie in contact with the inclined surfaces because they are pushed apart from one another by springs (not shown) here. A pin is inserted into a central bore 62 in the punch 60 on which the round body 19, with its centering bore 61, is centered in such a manner that a cavity 63 arises at its periphery into which the collar 29 can deform inwardly during the later rolling in. The outer shell 1 with the cylindrical collar 29 is pushed onto the round body 19 at the protruding punch 60. When the tool is moved together, the inserts 56 are at first lifted up above the protruding punch 60, the round body 19 and the outer shell 1, and it moves towards the center in accordance with the inclined surfaces. At the same time, a close pressing together of the round body and the outer shell arises, with a rolling in of the collar 29 commencing which is assisted by the retreat of the punch 60 through the lower form ring 59. The collar thus lays itself about the shoulder 5 of the later inner shell 2 under bias. When the tool is opened and the guide device is unlocked, the workpiece 1, 19 is released and it only remains necessary to carry out a chip forming machining of the round body 19 to the finished inner shell 2 with the bearing surface 21. Since the outer shell touches no metal parts except for the insulating plastic of the round body and is surrounded by heat insulating air when being pushed onto the round body 19, the outer shell can be pushed on in a preheated state, for example at a temperature of 200° C., and the tool moved together rapidly in order to cause the plastic to flow into cavities 23 of the outer shell.

The tools described here and the partial steps connected with them can also be used as independent manufacturing steps in other implants with thin walled metal sheets. Their use then relates to an implant with a thin walled metal sheet.

What is claimed is:

1. A twin-shelled artificial hip joint socket comprising:
    an outer shell of titanium and an inner shell of high molecular compressed polyethylene, with the outer shell including a portion that projects inwardly beyond the inner shell in the region of the equator to such an extent that a permanent, no longer releasable connection exists between the shells, wherein the outer shell is formed from a metal sheet of deep drawing grade with a thickness $3>s>1$ mm; wherein the outer shell is rolled in around a shoulder of the inner shell through a bending or rolling in process;
    wherein the outer shell has at least one protrusion approximately in a main load direction with an anchoring pin fastened thereto; and
    wherein the pin has a positioning tip penetrating up to and into the inner shell as a security against rotation by the inner shell.

2. An artificial hip joint socket in accordance with claim 1 wherein the metal sheet of deep drawing grade has a thickness $s=2$ mm.

3. An artificial hip joint socket in accordance with claim 1 wherein two anchoring pins are arranged parallel to one another.

4. An artificial hip joint socket in accordance with claim 1 wherein the protrusion has a bore with inner shoulders to which the pin is fastened from the inside by riveting, wherein the pin is pushed through from the outside.

5. An artificial hip joint socket in accordance with claim 1 wherein triangular teeth are pressed out on an outer shell by plastic deformation which have a cutting edge toward a pole and a flat side toward the equator of the outer shell.

6. A twin-shelled artificial hip joint socket comprising:
    an outer shell of titanium and an inner shell of high molecular compressed polyethylene, with the outer shell including a portion that projects inwardly beyond the inner shell in the region of the equator to such an extent that a permanent, no longer releasable connection exists between the shells, wherein the outer shell is formed from a metal sheet of deep drawing grade with a thickness $3>s>1$ mm; wherein the outer shell is rolled in around a shoulder of the inner shell through a bending or rolling in process;
    wherein the outer shell has at least one protrusion approximately in a main load direction with an anchoring pin fastened thereto; and
    wherein triangular teeth are pressed out on the outer shell by plastic deformation which have a cutting edge toward the pole and a flat side toward the equator of the outer shell.

7. A method for the manufacture of a hip joint socket wherein the hip joint socket comprises an outer shell of titanium and an inner shell of high molecular compressed polyethylene, with the outer shell projecting inwardly beyond the inner shell in a region of an equator to such an extent that a permanent, no longer releasable connection exists between the shells, wherein the outer shell in formed from a metal sheet of deep drawing grade with a thickness $3>s>1$ mm, wherein the outer shell in rolled approximately in a shoulder of the inner shell through a bending or rolling-in process, and wherein the outer shell has at least one protrusion approximately in a main load direction with an anchoring pin fastened thereto, the method comprising:
    producing an inner contour that corresponds to the inner shell up to a highest point on the equator, wherein the inner contour is cylindrical thereafter, the producing step being performed on a metal sheet of deep drawing grade with a thickness of $3>s>1$ mm;
    cutting off the outer shell in the cylindrical region;
    providing one or more protrusions on the outer shell with pressing tools wherein the one or more protrusions are provided with shoulders;
    forming bores in the protrusions;
    inserting anchoring pins with a projecting head into the bores and riveting the anchoring pins from within;
    pressing into the outer shell a round body of plastic whose outer contour corresponds to the contour of the inner shell while at the same time the edge of the outer shell is deformed through a bending or rolling-in process in the direction toward its polar axis in order to produce a firm, non-releasable connection; and inserting at the outer shell a workpiece consisting of the outer shell and the round body in order to machine the round body to the inner shell with a bearing surface by chip forming machining.

8. A method in accordance with claim 7 wherein triangular teeth are pressed out from the outer shell with a pressing tool in an intermediate step prior to the fourth step at the latest.

9. A method in accordance with claim 7 wherein a mesh of titanium wire, which corresponds to the form of the outer shell and covers over the outer shell in a certain region, is fastened to the outer shell by welding in an intermediate step.

10. A method in accordance with claim 7 wherein the metal sheet has a thickness of 2 mm.

11. A method on accordance with claim 7 wherein the round body of plastic consists of high molecular compressed polyethylene.

* * * * *